(12) United States Patent
Galiano

(10) Patent No.: US 12,265,021 B2
(45) Date of Patent: Apr. 1, 2025

(54) METHOD AND SYSTEM TO IDENTIFY MICROORGANISMS

(71) Applicant: ALIFAX S.R.L., Polverara (IT)

(72) Inventor: Paolo Galiano, Padua (IT)

(73) Assignee: ALIFAX S.R.L., Polverara (IT)

( * ) Notice: Subject to any disclaimer, the term of this patent is extended or adjusted under 35 U.S.C. 154(b) by 765 days.

(21) Appl. No.: 17/623,240

(22) PCT Filed: Jul. 30, 2019

(86) PCT No.: PCT/IT2019/000062
§ 371 (c)(1),
(2) Date: Dec. 27, 2021

(87) PCT Pub. No.: WO2021/019581
PCT Pub. Date: Feb. 4, 2021

(65) Prior Publication Data
US 2022/0364985 A1    Nov. 17, 2022

(51) Int. Cl.
*G01N 21/35* (2014.01)
*G01N 21/65* (2006.01)
*G16B 50/00* (2019.01)

(52) U.S. Cl.
CPC .......... *G01N 21/35* (2013.01); *G01N 21/658* (2013.01); *G16B 50/00* (2019.02)

(58) Field of Classification Search
CPC .......... G01N 2021/3595; G01N 21/35; G01N 21/552; G01N 21/658; G01N 2201/129; G16B 50/00
See application file for complete search history.

(56) References Cited

U.S. PATENT DOCUMENTS

| | | | |
|---|---|---|---|
| 5,660,998 A | 8/1997 | Naumann et al. | |
| 6,379,920 B1 | 4/2002 | El-Sayed et al. | |
| 9,551,654 B2 | 1/2017 | Ismail et al. | |
| 2014/0377795 A1 | 12/2014 | Gannot et al. | |
| 2017/0073725 A1* | 3/2017 | Upton | G01N 21/33 |
| 2017/0167973 A1 | 6/2017 | Ismail et al. | |

FOREIGN PATENT DOCUMENTS

| | | |
|---|---|---|
| CN | 103217398 A | 7/2013 |
| EP | 2 439 536 A1 | 4/2012 |
| WO | WO-2006/002537 A1 | 1/2006 |
| WO | WO-2017/210783 A1 | 12/2017 |
| WO | WO-2019/150408 A1 | 8/2019 |

OTHER PUBLICATIONS

Sousa et al., "Discrimination of the Acinetobacter calcoaceticus-Acinetobacter baumanii complex species by Fourier transform infrared spectroscopy," European Journal of Clinical Microbiology & Infectious Diseases, vol. 33, No. 8, pp. 1345-1353, 2014.

(Continued)

*Primary Examiner* — Jennifer Wecker
(74) *Attorney, Agent, or Firm* — MARSHALL, GERSTEIN & BORUN LLP

(57) ABSTRACT

A method of identifying microorganisms in a sample by evaluating the vibrational profile.

10 Claims, 4 Drawing Sheets

(56) References Cited

OTHER PUBLICATIONS

Udelhoven et al., "Development of a Hierarchical Classification System with Artificial Neural Networks and FT-IR Spectra for the Identification of Bacteria," Applied Spectroscopy, vol. 54, No. 10, pp. 1471-1479, 2000.
Whittaker et al., "Identification of foodborne bacteria by infrared spectroscopy using cellular fatty acid methyl esters," Journal of Microbiological Methods, vol. 55, No. 3, pp. 709-716, 2003.
International Search Report and Written Opinion for PCT/IT2019/00062, mailed Apr. 2, 2020.

\* cited by examiner

Fig. 5

|  | \ | PREDICTED | | | | | | | | | | | | | | | | | | | | |
|---|---|---|---|---|---|---|---|---|---|---|---|---|---|---|---|---|---|---|---|---|---|---|
| | | Acinetobacter | Burkholderia | Candida | Citrobacter | Corynebacterium | Enterobacter | Enterococcus | Escherichia | Haemophilus | Klebsiella | Moraxella | Morganella | Proteus | Providencia | Pseudomonas | Serratia | Staphylococcus | Stenotrophomonas | Streptococcus | Total |
| ACTUAL | Acinetobacter | 100% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 313 |
| | Burkholderia | 0.0% | 100% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 111 |
| | Candida | 0.0% | 0.0% | 100% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 1716 |
| | Citrobacter | 0.0% | 0.0% | 0.0% | 100% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 325 |
| | Corynebacterium | 0.0% | 0.0% | 0.0% | 1.7% | 100% | 0.0% | 0.0% | 0.0% | 0.0% | 0.0% | 0.0% | 0.0% | 0.0% | 0.0% | 0.0% | 0.0% | 0.0% | 0.0% | 0.0% | 145 |
| | Enterobacter | 0.0% | 0.0% | 0.0% | 0.0% | 0.0% | 97.5% | 0.0% | 0.0% | 0.0% | 0.0% | 0.0% | 0.0% | 0.0% | 0.0% | 0.0% | 0.0% | 0.0% | 0.0% | 0.0% | 121 |
| | Enterococcus | 0.0% | 0.0% | 0.0% | 0.0% | 0.0% | 0.0% | 100% | 0.0% | 0.0% | 0.0% | 0.0% | 0.0% | 0.0% | 0.0% | 0.0% | 0.0% | 0.0% | 0.0% | 0.0% | 259 |
| | Escherichia | 0.0% | 0.0% | 0.0% | 0.0% | 0.0% | 0.0% | 0.0% | 99.2% | 0.0% | 0.8% | 0.0% | 0.0% | 0.0% | 0.0% | 0.0% | 0.0% | 0.0% | 0.0% | 0.0% | 123 |
| | Haemophilus | 0.0% | 0.0% | 0.0% | 0.0% | 0.0% | 0.0% | 0.0% | 0.0% | 100% | 0.0% | 0.0% | 0.0% | 0.0% | 0.0% | 0.0% | 0.0% | 0.0% | 0.0% | 0.0% | 56 |
| | Klebsiella | 0.0% | 0.0% | 0.0% | 0.0% | 0.0% | 0.0% | 0.0% | 0.0% | 0.0% | 100% | 0.0% | 0.0% | 0.0% | 0.0% | 0.0% | 0.0% | 0.0% | 0.0% | 0.0% | 488 |
| | Moraxella | 0.0% | 0.0% | 0.0% | 0.0% | 0.0% | 0.0% | 0.0% | 0.0% | 0.0% | 0.0% | 100% | 0.0% | 0.0% | 0.0% | 0.0% | 0.0% | 0.0% | 0.0% | 0.0% | 160 |
| | Morganella | 0.0% | 0.0% | 0.0% | 0.0% | 0.0% | 0.0% | 0.0% | 0.0% | 0.0% | 0.0% | 0.0% | 100% | 0.0% | 0.0% | 0.0% | 0.0% | 0.0% | 0.0% | 0.0% | 173 |
| | Proteus | 0.0% | 0.0% | 0.0% | 0.0% | 0.0% | 0.0% | 0.0% | 0.0% | 0.0% | 0.0% | 0.0% | 0.0% | 100% | 0.0% | 0.0% | 0.0% | 0.0% | 0.0% | 0.0% | 343 |
| | Providencia | 0.0% | 0.0% | 0.0% | 0.0% | 0.0% | 0.0% | 0.0% | 0.0% | 0.0% | 0.0% | 0.0% | 0.0% | 0.0% | 100% | 0.0% | 0.0% | 0.0% | 0.0% | 0.0% | 225 |
| | Pseudomonas | 0.0% | 0.0% | 0.0% | 0.0% | 0.0% | 0.0% | 0.0% | 0.0% | 0.0% | 0.0% | 0.0% | 0.0% | 0.0% | 0.0% | 100% | 0.0% | 0.0% | 0.0% | 0.0% | 260 |
| | Serratia | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 100% | 0.0% | 0.0% | 0.0% | 119 |
| | Staphylococcus | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 100% | 0.0% | 0.0% | 1189 |
| | Stenotrophomonas | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 100% | 0.0% | 143 |
| | Streptococcus | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 99.9% | 1486 |
| | Total | 313 | 111 | 1716 | 327 | 145 | 118 | 259 | 123 | 56 | 489 | 160 | 173 | 344 | 225 | 260 | 119 | 1189 | 143 | 1485 | 7755 |

METHOD AND SYSTEM TO IDENTIFY MICROORGANISMS

FIELD OF THE INVENTION

The present invention concerns a method to identify microorganisms, applicable in the medical, clinical, veterinary, agriculture and food, and environmental fields, which uses statistical techniques, such as for example methods for multivariate analysis of spectral profiles, or alternatively neural networks, to identify and obtain indications relating to the growth of microorganisms in extremely short times compared to conventional methods.

In particular, the invention supplies an analytical instrument to identify microorganisms through the analysis of the spectral profile of a vibrational spectrum of an unknown sample, and the comparison of the spectral profile with spectra of samples previously collected and memorized in a database.

BACKGROUND OF THE INVENTION

The use of vibrational spectroscopy techniques to identify microorganisms is known.

For example, Fourier transform infrared spectroscopy (FTIR) is a non-destructive analysis technique, which allows to obtain information on the chemical composition of a sample analyzed. Since the beginning of the 1990s this technique has been used for the analysis of biological samples (Diem M. et al., The Analyst [27 Aug. 2004, 129 (10): 880-885]).

At the same time, the ability of the FTIR technique to identify and classify unknown microorganisms was shown (Helm D. et al., Journal of General Microbiology (1991, 137, 69-79) and Marley L. et al., Vibrational Spectroscopy 26, 2, 2001, 151-159).

It is known that the different species, subspecies or sub-classifications of microorganisms are characterized by a precise biochemical composition, in terms of proteins, lipids, nucleic acids and polysaccharides, which is reflected in a distinct vibrational spectrum (ed. Griffiths and Chalmers, 2001 Handbook of vibrational spectroscopy, John Wiley & sons, New York, Volume 5).

Some potential applications suggested by the FTIR technique in microbiology include:
(i) identification of pathogens in the human or veterinary field, for example in a clinical laboratory;
(ii) epidemiological investigations, topic of study, screening of pathogens, hygiene checks, elucidation of infectious chains, control therapies and detection of recurrent infections;
(iii) characterization and screening of microorganisms from the environment;
(iv) monitoring of biotechnological processes;
(v) microbiological quality control in food or pharmaceutical industries;
(vi) maintenance of harvested strains.

Methods to identify microorganisms are known, based on techniques of comparative analysis between the spectrum of an unknown sample and the spectra of known species of microorganisms, stored in a database.

Examples of known identification methods of this type are reported in documents U.S. Pat. No. 5,660,998A, CN103217398A, U.S. Pat. No. 6,379,920B1, WO2006002537A1, U.S. Pat. No. 9,551,654B2, US20170167973A1, WO2017/210783A1, Sousa et al., European Journal of Clinical Microbiology & Infectious Diseases (2014) 33: 1345-1353, Whittaker et al., Journal of Microbiological Methods 55 (2003) 709-716, Wang et al., International Journal of Food Microbiology 167 (2013) 293-302.

Another method has been described in patent application PCT/IT2019/050025 in the name of the Applicant.

In many of the known methods, however, spectra acquisition is performed in transmission, reflection, or imaging modes.

For example, transmission or reflection acquisition modes are reported in U.S. Pat. Nos. 5,660,998 and 6,379,920, while imaging modes are adopted in WO2006002537A1, U.S. Pat. No. 9,551,654B2, US20170167973A1.

These methods have disadvantages connected to the fact that the signal obtained directly depends on the thickness and morphology of the sample, which may be too thick and generate saturation, or non-homogeneous and generate distortions due to scattering.

It is also known that methods based on imaging approaches, for example multipixel, may have limitations on the resolution of the individual spectra, due to the lower signal/noise ratio obtainable per pixel, compared to single-point detectors.

Another disadvantage of the state of the art is that often the spectra can present signals due to the presence of water or other contaminants, which cover the peculiar signals of the microorganisms.

In some cases, such as for example CN103217398A, drying procedures are adopted but, as reported in WO 2017/210783A1, these procedures can have damaging and irreversible effects on the microorganisms, also modifying their spectra.

In some cases, such as for example WO 2017/210783 A1, it is possible to resort to multiple acquisitions to remove the water components present in the spectra. However, this solution has disadvantages connected to greater analysis time and greater complexity of the analytical procedures for comparing spectra.

Another disadvantage of the state of the art is that often the reference database comprises a limited number of species of microorganisms, and therefore does not cover a wide range of possible species.

By way of example, the database and the related identification method reported in CN103217398A refer to 13 bacterial species.

Moreover, with the increase in sizes of the reference databases, a series of problems comes into being relating to the procedures for cultivating and growing the species of microorganisms, to the procedures for acquiring the spectra and to the comparative analysis procedures.

For example, as the size of the database increases, the analysis time of the unknown sample also increases, given that the spectrum of the unknown sample must be compared with a large number of spectra contained in the database.

Moreover, the same species of microorganisms can have a great variability in the spectral characteristics, making it difficult to compare them with the spectra contained in the database.

This variability may be due to the presence of different strains for each species, or to differences between different cultures of the same species due to possible variations in the chemical composition of the culture medium and/or growth conditions.

There is therefore the need to develop new methods to identify microorganisms that can work for a large number of classifications of microorganisms (for example taxonomic categories or phenotypic groups or genotypic groups), and with a great variability of the reference database.

One purpose of the present invention is therefore to propose an identification method that is able to determine whether samples of unknown microorganisms belong to one or more categories and/or groups as above.

Another purpose of the present invention is to propose a method to identify microorganisms that can differentiate different strains of the same species, subspecies or subclassification of microorganisms, possibly grown in different cultures on different media, or in different environmental conditions in the presence or absence of biological fluids and/or complex matrixes.

Another purpose of the present invention is to supply a method to identify microorganisms that is accurate, that requires rapid times for each individual analysis and that does not require high computing power, even in the case of large databases.

Another purpose of the present invention is to supply an apparatus which can implement the method to identify microorganisms in a simple manner, integrating all the different steps of analysis and instrumental components.

Another purpose of the present invention is to supply an apparatus and a method which do not require continuous or partial internet connection for remote data processing and consequent achievement of the result.

The Applicant has devised, tested and embodied the present invention to overcome the shortcomings of the state of the art and to obtain these and other purposes and advantages.

SUMMARY OF THE INVENTION

The present invention is set forth and characterized in the independent claims. The dependent claims describe other characteristics of the invention or variants to the main inventive idea.

The present invention concerns a method to identify microorganisms, and in particular a method to allow the identification of microorganisms present in an unknown sample, comparing the vibrational spectrum of said unknown sample with pre-calculated models created from reference vibrational spectra of known samples, which have been previously archived in a database.

The method to identify microorganisms according to the present invention comprises:
 a step of preparing a database of reference spectra of samples of known microorganisms;
 one or more steps of creating a plurality of pre-calculated models, associated with categories and/or classification groups of hierarchically organized microorganisms, from broader categories and/or classification groups to smaller categories and/or classification groups, each pre-calculated model comprises identification spectral characteristics associated with a category and/or a classification group of microorganisms;
 one step of sampling an unknown sample;
 one or more steps of acquiring the spectrum of the unknown sample;
 one or more steps of processing the spectrum of the unknown sample;
 one or more analysis steps, each of which provides to perform in succession a plurality of sub-steps of comparing the spectrum of the unknown sample with said pre-calculated models, each sub-step comparing, with multivariate analysis methods, the spectrum of the unknown sample with the pre-calculated models of progressively smaller categories and/or classification groups, in order to supply at least scores showing the belonging of the unknown sample to the categories and/or classification groups of microorganism.
 one or more control steps in which a new acquisition step of the spectrum of the unknown sample is requested if the reliability parameters are lower than predetermined acceptance values, or a final result of the method is supplied, which can comprise a failed identification, or a successful identification.

In some embodiments, the step of preparing a database of reference spectra associated with known microorganism samples provides, for each known sample:
 a step of sampling the known sample, possibly obtained from growth on solid or liquid media in the presence or absence of biological fluids and/or complex matrices;
 one or more steps of acquiring the spectrum of the known sample;
 one or more steps of processing the spectrum of the known sample.

The unknown sample and/or the known sample can be, in a first embodiment of the method, a sample obtained from growth using any suitable medium whatsoever, for example solid or liquid, possibly in the presence or absence of biological fluids and/or complex matrices.

In another embodiment, the unknown sample and/or the known sample can be directly obtained from native samples without being subjected to the growth phase.

In some embodiments, the step of preparing the database can be carried out only once to create the database, which can then be used for each subsequent analysis of unknown samples.

In some embodiments, the step of preparing the database can also refer to the database update, to be carried out whenever it is desired to include new categories and/or classification groups of microorganism, thus extending the range of applicability of the method.

Similarly, the pre-calculated models, once created, can be used for every subsequent analysis of unknown samples, or can also be updated every time it is desired to add new categories and/or classification groups of microorganism.

According to the present invention, the spectra are acquired by means of an apparatus able to detect the absorption of infrared radiation in a direct or indirect manner, such as for example a vibrational spectrophotometer.

In some embodiments, the invention can use a continuous signal acquisition mode both in the absence and also in the presence of a sample, the continuous mode assisting respectively the cleaning operations of the instrument and the objective evaluation of the spectral parameters (for example signal intensity, signal-to-noise ratio, spectral shape, optimum drying level) preparatory to the acquisition of the spectrum.

Advantageously, according to the present invention, the monitoring of the spectral parameters as above is provided, this allowing to standardize the quality of the spectra obtained making the process independent of subjective evaluations by the operator.

The spectra acquired with this mode therefore refer to samples that have substantially the same levels of intensity and drying, and are therefore more comparable to each other.

In some embodiments, the present invention provides to use algorithms which automatically identify the most significant identification spectral characteristics for the classification groups.

This characteristic allows to significantly reduce the time required by the analysis step, allowing to speed up the times and increase the accuracy of the identification.

Advantageously, with respect to the methods of the state of the art, the sequential use of a plurality of pre-calculated models associated with classification groups of hierarchically organized microorganisms, allows to reduce the computing power necessary for the identification of an unknown sample, therefore not requiring the use of an Internet connection which is instead necessary if using distributed or remote computing systems for data processing.

These characteristics allow to increase the size of the database, allowing to identify many species, subspecies, classifications or sub-classifications of different microorganisms, of different strains of the same species, subspecies or subfamily, also possibly grown in different cultures on different media, or in different environmental conditions, possibly in the presence of biological fluids and/or complex matrices.

The present invention also concerns an apparatus to carry out the method to identify microorganism described here, comprising a device to detect the vibrational profile, comprising a source of radiation, a detector, an acquisition zone being defined on which the sample to be analyzed is positioned, and an electronic device, of the fixed or portable type, coupled to the detection device, in which a processing system and a data display system are installed.

In some embodiments, pre-calculated models are stored in the electronic device, which are associated with classification groups of hierarchically organized microorganisms, from broader classification groups to smaller classification groups, each pre-calculated model comprising identification spectral characteristics associated with a category and/or classification group of microorganisms.

ILLUSTRATION OF THE FIGURES

These and other aspects, characteristics and advantages of the present disclosure will be understood with reference to the following description, drawings and attached claims. The drawings, which are an integral part of the description, show some embodiments of the present invention and, together with the description, propose to describe the principles of the disclosure.

The present invention is described and shown better with the aid of the following drawings, in which:

FIG. 3a shows the raw data collected, wherein each species is represented by a different color, while FIG. 3b shows the data transformed;

FIG. 5 is a confusion matrix obtained by the validation through cross validation of the method according to the embodiments described here with the spectra of the database and used to evaluate the classification of the microorganisms according to the "Genus" category.

To facilitate comprehension, the same reference numbers have been used, where possible, to identify identical common elements in the drawings. It is understood that elements and characteristics of one embodiment can conveniently be incorporated into other embodiments without further clarifications.

DESCRIPTION OF EMBODIMENTS

We will now refer in detail to the various embodiments of the present invention, of which one or more examples are shown in the attached drawings. Each example is supplied by way of illustration of the invention and shall not be understood as a limitation thereof. For example, the characteristics shown or described insomuch as they are part of one embodiment can be adopted on, or in association with, other embodiments to produce another embodiment. It is understood that the present invention shall comprise all such modifications and variants.

Before describing these embodiments, we must also clarify that the present description is not limited in its application to details of the construction and disposition of the components as described in the following description using the attached drawings. The present description can provide other embodiments and can be obtained or executed in various other ways. We must also clarify that the phraseology and terminology used here is for the purposes of description only, and cannot be considered as limitative.

Unless otherwise defined, all the technical and scientific terms used here and hereafter have the same meaning commonly understood by a person of ordinary experience in the field to which the present invention belongs.

Although methods and materials similar or equivalent to those described here may be used in practice or in the tests to verify this disclosure, the methods and materials are described below by way of example. In the event of conflict, the present application, comprising the definitions, shall prevail. The materials, methods and examples are purely illustrative and must not be understood in a restrictive manner.

Here and hereafter, by sample we mean a minimum quantity of any substance whatsoever containing microbial organisms, such as for example microorganisms, but not only, for analysis purposes.

Sometimes, if necessary, we will specify unknown sample or known sample, in cases where the composition of microorganisms is, respectively, unknown or known.

In some embodiments, the microorganisms can be of medical, clinical, veterinary, agriculture and food, environmental interest.

Figure 1:
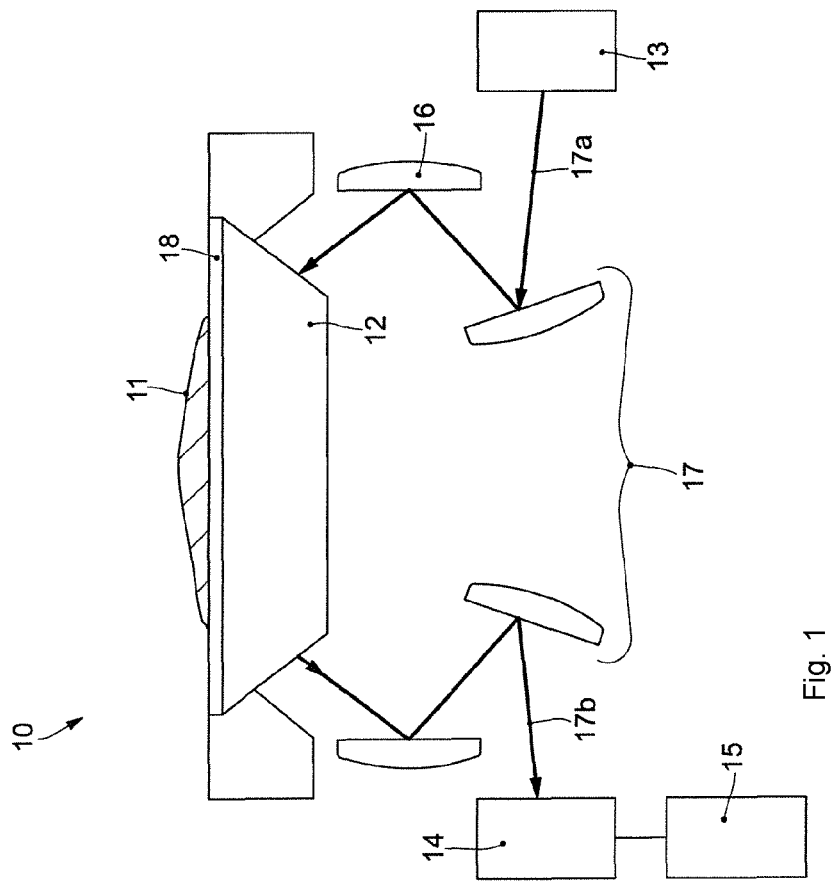
FIG. 1 is a schematic representation of a possible apparatus in accordance with the method of the present invention.

FIG. 1 schematically shows an apparatus 10 to identify microorganisms in accordance with the present invention.

In some embodiments, for the detection, direct or indirect, of the absorption of infrared radiation the apparatus uses a device such as, for example:

an Infrared IR spectrophotometer, possibly operating in Fourier-Transform InfraRed
a Raman spectrometer,
a photothermal spectrometer
a photoacoustic spectrometer
the coupling of one of the instruments listed above with resonant techniques and not for signal elevation, such as resonant Raman, Surface Enhanced, Surface Enhanced Raman Spectroscopy (SERS), Surface Enhanced InfraRed Absorption (SEIRA), Resonant Surface Enhanced InfraRed Absorption (resonant SEIRA), Tip-enhanced Raman spectroscopy (TERS).

The applicability of the present invention is not in fact limited by the type of technique used to acquire the vibrational profile of the unknown sample, and the method and apparatus described here can be used in association with any type of vibrational spectra whatsoever.

By way of example, this apparatus comprises a spectrophotometer for FTIR-type vibrational spectroscopy, which can use any mode of acquisition of the vibrational spectrum of samples, such as for example the ATR (Attenuated Total Reflectance) and therefore be an FTIR-ATR spectrophotometer (FIG. 1).

The spectrophotometer can be coupled with a processing system and a data display system.

The processing system and the display system can, for example, be integrated into a single processing and display system and/or can be comprised in an electronic device 15, such as for example a personal computer equipped with a screen or a portable device such as a cellular phone or tablet.

In some embodiments, the processing system comprises a computer program, which can be memorized in a medium readable by an electronic device 15 and which contains instructions that can be executed on each occasion by the apparatus 10.

Hereafter, for simplicity of exposition, reference will be made to the electronic device 15 to indicate the set of software and hardware systems able to manage the apparatus 10, and to process and display the data.

The spectrophotometer, known per se in its main components, comprises at least a source 13 of radiation 17 and a detector 14.

For simplicity, other components of the spectrophotometer, such as mono-chromator, chopper, interferometer, have not been shown in FIG. 1.

The source 13 can emit any type of radiation 17 suitable to excite the molecules present in the sample, for example, in the case of an IR, FTIR or FTIR-ATR spectrophotometer, it can be a source of infrared radiation 17.

In some embodiments, the source 13 can be a black body source of the Globar type, or a Quantum Cascade Laser (QCL) or a generic laser with emission in the infrared region.

In some embodiments, for example if the spectrophotometer is based on Raman techniques, the source 13 can be a laser source 13 of monochromatic light, possibly with frequencies associated with the infrared region or even higher, based on the particular type of Raman technique employed.

In some embodiments, the radiation 17 emitted by the source 13, that is, the incident radiation 17a, can be directed, possibly by means of reflecting elements 16, toward the sample, positioned in an acquisition zone 18.

In embodiments in which the ATR mode is used, the incident radiation 17a can be directed by the reflective elements 16 to effect an internal reflection element.

In some embodiments, the internal reflection element can be, for example, a crystal 12.

In some embodiments, the crystal 12 can be a crystal 12 with a high refraction index.

In some embodiments, the crystal 12 can be a crystal 12 of diamond, ZnSe, silicon or germanium.

Advantageously, if the crystal 12 is a diamond crystal 12, it has the advantages of being more durable than ZnSe, silicon or germanium, used in comparable measurements, and of having a greater transparency range.

The reflection of the radiation 17 inside the crystal 12 produces an evanescent field on the surface of the crystal 12, on which the acquisition zone 18 can be defined.

This evanescent field can penetrate for a range of depths that, depending on the case, can reach up to a few microns inside the sample.

In particular, this range of depths is a function of the angle of incidence and the wavelength of the incident radiation 17a, as well as of the refractive index of the material used for the crystal 12, and therefore can be considered substantially constant for all the samples analyzed.

For this reason, advantageously, the ATR mode allows to acquire spectra independent of the optical path of radiation through the sample, and therefore independent of the thickness of the sample, guaranteeing a higher reproducibility compared to approaches that use transmission or reflectance.

Moreover, this mode allows to limit or prevent phenomena of scattering and/or signal saturation that can negatively affect the quality of the spectrum.

This mode therefore guarantees greater repeatability of the measurement and a simpler preparation of the sample.

The radiation 17 at exit, after the interaction with the sample, that is, the outgoing radiation 17b, is then directed by the reflecting elements 16 toward the detector 14.

In some embodiments, the detector 14 can be a DLaTGS detector (Deuterated L-alanine doped triglycine sulphate).

In alternative embodiments, the detector 14 can be a DTGS detector. In alternative embodiments, the detector 14 can be an MCT (Mercury Cadmium Telluride) detector, single or disposed in an array.

In alternative embodiments, the detector 14 can be a CCD detector.

In alternative embodiments, the detector can be a bolometer or microbolometer, single or disposed in an array.

By way of example, the detector 14 transforms the optical information contained in the outgoing radiation 17b into electric signals, which are sent to the electronic device 15.

In some embodiments, the apparatus is disposed to acquire spectra in the region NIR (Near IR) and/or MIR (Mid IR) and/or FIR (Far IR).

In some embodiments, the apparatus 10 can operate in continuous acquisition mode, that is, displaying on the screen of the electronic device 15 in real time what is acquired on each occasion in the acquisition zone 18.

Figure 2:
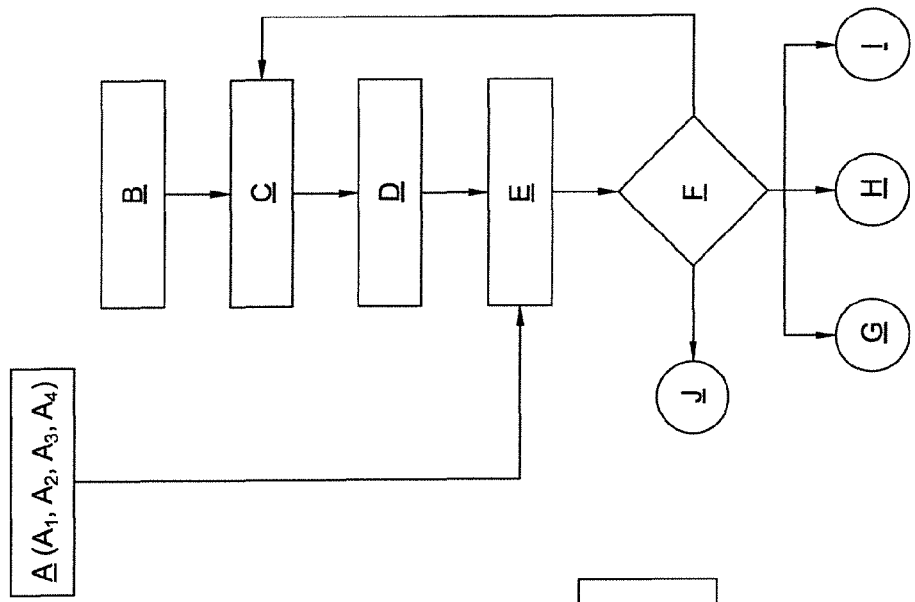
FIG. 2 shows a block diagram in which the steps of one embodiment of the method of the present invention as shown by way of example.

The present invention also concerns a method to identify microorganisms, in a sample by evaluating the vibrational profile, shown schematically in FIG. 2 and comprising:

a step A of preparing a database of reference spectra of known samples of known microorganisms comprising:
one or more steps A1 of sampling a known sample;
one or more steps A2 of acquiring the spectrum of the known sample;
one or more steps A3, possibly automated, of processing the spectrum of the known sample in order to at least identify spectral regions, in which to evaluate the presence of identification spectral characteristics of each category and/or classification group.
one or more steps A4 of creating a plurality of pre-calculated models, associated with categories and/or classification groups of hierarchically organized microorganisms, from broader categories and/or classification groups to smaller categories and/or classification groups, each pre-calculated model comprising identification spectral characteristics associated with a category and/or a classification group of microorganisms;
a step B of sampling an unknown sample;
one or more steps C of acquiring the spectrum of the unknown sample;

one or more steps D of processing the spectrum of the unknown sample on the basis of what defined in step A3 one or more analysis steps E, each of which provide to perform in succession a plurality of sub-steps of comparing the spectrum of the unknown sample with said pre-calculated models, each sub-step comparing, by means of multivariate analysis methods, the spectrum of the unknown sample with the pre-calculated models of progressively smaller categories and/or classification groups, in order to supply at least scores showing the belonging of the unknown sample to said categories and/or classification groups of microorganism.

one or more control steps F in which a new acquisition step of the spectrum C of the unknown sample is requested if said reliability parameters are lower than predetermined acceptance values, or a final result of the method is supplied, which can comprise a failed identification J, or a successful identification G, H, I.

In some embodiments, said steps A1, A2, A3 can be repeated whenever it is desired to insert a new known sample in the database.

In some embodiments, in the sampling steps B, A1, the sample can be subjected to preliminary procedures, which provide the addition of nutrient substances for the microorganisms.

In some embodiments, the sample can be grown on a solid culture medium.

In some embodiments, the sample can be grown on Petri dishes.

In some embodiments, the sample can be grown on liquid culture media and then centrifuged, obtaining a concentrated pellet.

In some embodiments, the sample can be grown on liquid culture media, or liquid growth broth, and then filtered.

In some embodiments, the sample can be grown on liquid culture media, or liquid growth broth, or it can be subjected to concentration or enrichment procedures to increase the concentration of microorganisms present.

In other embodiments the sample under analysis can be directly obtained from a native sample without undergoing a growth phase.

In some embodiments, the sample can possibly contain biological fluids and/or complex matrices, of human, animal, environmental, agriculture and food origin. In some embodiments, the spectrum acquisition steps C, A2 can provide a preliminary step of cleaning the surfaces of the device in contact with the sample, for example of the acquisition zone 18 shown in FIG. 1.

In some embodiments, it is possible to acquire background spectra, for example by means of continuous acquisition mode, to verify the effectiveness of such cleaning, for example by observing the disappearance of absorption bands linked to the impurities deposited on the acquisition zone 18.

In some embodiments, the spectrum acquisition steps C, A2 also provide that an assay of the sample is taken and deposited on the acquisition zone 18, possibly positioned on the crystal 12 of the spectrophotometer.

In some embodiments, the assay is deposited on the acquisition zone 18 in a solid form, for example by removing and depositing it by means of a disposable rod.

In some embodiments, the assay can be pressed against the acquisition zone 18, for example by using a dynamometric press.

In some embodiments, the level of drying of the sample and the spectral parameters (for example signal intensity, signal-to-noise ratio, spectral shape) preparatory to the acquisition of the spectrum are spectroscopically monitored.

In some embodiments, it is possible to evaluate the water content leaving the apparatus in continuous acquisition mode and monitoring the reduction, up to a possible complete disappearance, of the absorption bands relating to the spectral characteristics of the water in the respective ranges of wave numbers.

According to the present invention, the spectrum of the sample is acquired when a predetermined standard level of drying and spectral parameters are reached.

Advantageously, this characteristic allows to overcome or at least limit the problem of the state of the art whereby the spectra can have signals due to the presence of water that cover, or interfere with, the peculiar signals of the microorganisms.

The spectrum acquisition steps C, A2 also provide that the spectrum of the assay taken from the sample is recorded.

In some embodiments, spectrum recording provides to acquire a predetermined number of sequential spectra, which are then averaged to improve the signal to noise ratio.

In some embodiments, a number of spectra comprised in a range from 8 to 512 for each assay can be acquired and averaged, preferably between 32 and 256 for each assay, even more preferably between 64 and 128 for each assay.

Figure 3A:
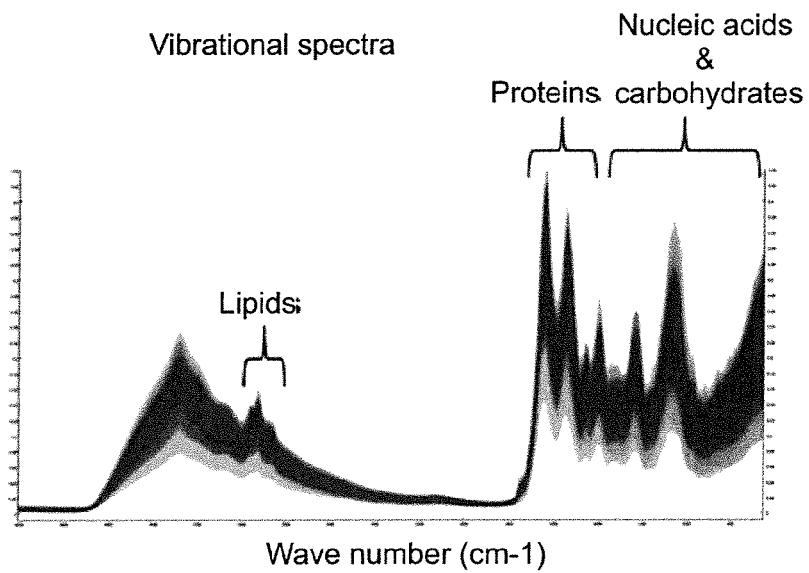
FIGS. 3a and 3b show experimental data collected using the FTIR-ATR technique, where
Figure 3B:
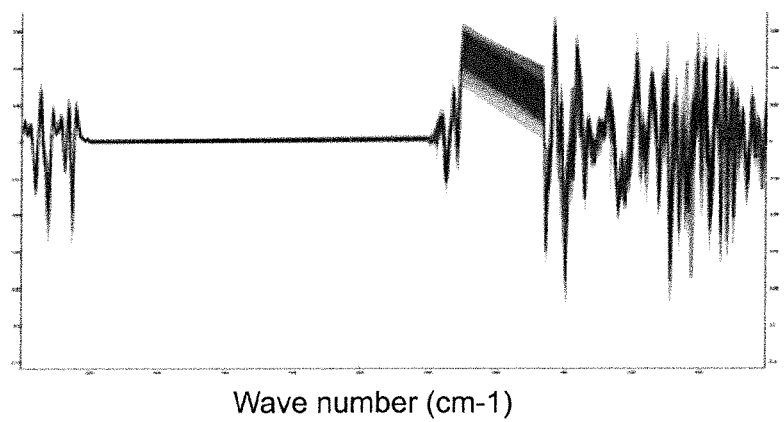

The steps D, A3 of processing the spectrum, or the average of the spectra, can provide:

the identification, possibly automated, of spectral regions in which to evaluate the presence of spectral characteristics identifying each category and/or classification group;

to use linear and/or non-linear interpolation and/or fitting algorithms of the spectral profiles;

to calculate the first and/or second derivative of the spectral profile;

to normalize the derivatives using a vector normalization algorithm over the entire spectral range. By way of example, FIG. 3*a* shows the spectra that can be collected for different samples, while FIG. 3*b* shows the processed spectra.

By repeating steps A1, A2, A3 for several known samples, it is possible to prepare the database of reference spectra of known microorganisms.

However, in some embodiments of the present method it is also provided that the database can comprise spectra of known microorganisms obtained using other methods.

In some embodiments, the database comprises spectra relating to monomicrobial cultures belonging to different classification groups of known microorganisms.

In some embodiments, the database comprises spectra relating to different strains of known microorganisms for each category and/or classification group.

In some embodiments, the database comprises spectra relating to samples grown on culture media, for example but not only Agar, CNA Agar, CLED Agar, Blood Agar, Chromogenic Agar, Sabouraud Agar.

In some embodiments, the database comprises spectra relating to samples grown in a liquid-phase growth broth, which are then centrifuged, or filtered, or enriched, to obtain pellets or concentrated samples.

In some embodiments, the database comprises spectra relating to samples obtained without a growth phase, that is, obtained from native samples, directly from any substance or material whatsoever.

Advantageously, measurements of spectra obtained from growth in liquid broth and subsequent pelletizing or filtration or enrichment allow to identify the spectra directly in the presence of biological fluids, for example bodily fluids, and/or complex matrices.

This heterogeneity and variability of the spectra contained in the database allows to perform a general analysis, which allows to identify the microorganisms, also including effects deriving from growths on different culture media.

In the embodiments where multiple acquisitions of each spectrum are used, it is possible to insert in the database the individual spectra repeated and/or the average spectrum calculated on the repetitions.

Step A4 provides to create, starting from the spectra contained in the database, pre-calculated models, that is, reference libraries that comprise identification spectral characteristics associated with classification groups of hierarchically organized microorganisms.

In some embodiments, the pre-calculated models can be stored in the electronic device 15 of the apparatus 10.

In some embodiments, the identification spectral characteristics can, for example, comprise shapes, sizes, intensities and areas of the peaks, correlations and ratios between the intensities or between the areas of different peaks, frequencies of the maximum values of the peaks.

In some embodiments, the identification spectral characteristics can comprise the spectral profiles in the spectral zones between 950 and 1280 $cm^{-1}$ (associated with nucleic acids, carbohydrates and polysaccharides), between 1280 and 1480 $cm^{-1}$ (associated with starches, for example of proteins, methyl and methylene, for example of lipids), between 1700 and 1800 $cm^{-1}$ (associated with carbonyl groups, for example of lipids), between 2800 and 3000 $cm^{-1}$ (associated with aliphatic chains, for example of lipids), shown by way of example in FIGS. 3a and 3b.

In some embodiments, the classification groups can comprise taxonomic categories such as for example domain, kingdom, phylum, class, order, family, tribe, genus, species, subspecies.

In some embodiments, the classification groups can for example be prokaryotes, eukaryotes, archaea, Gram-positive bacteria, Gram-negative bacteria, yeasts, filamentous fungi.

In further embodiments, the classification groups can, for example, be taxonomic categories and/or phenotypic groups and/or genotypic groups.

In some embodiments, the classification groups can be hierarchically organized from broader classification groups to smaller classification groups, so that the broader classification groups comprise a set of smaller classification groups, for example one genus of microorganisms can include different species, and one species of microorganisms can include several subspecies.

In some embodiments, the pre-calculated models can comprise a list of identification spectral characteristics relevant for each category and/or classification group.

In step A4, the spectra contained in the database are then compared in order to identify the identification spectral characteristics common to the classification groups of microorganisms.

In some embodiments, an automatic recognition system can be provided to identify the identification spectral characteristics associated with the classification groups.

In some embodiments, the identification spectral characteristics associated with the classification groups can be identified by means of the statistical analysis techniques mentioned below and/or approaches based on neural networks and/or artificial learning.

In some embodiments, an arbitrary number of pre-calculated models can therefore be created, based on the classification groups.

In this way, every time that, in analysis step E, the spectrum of the unknown sample is compared with the model, this comparison can be performed only in the spectral intervals and/or in relation to the spectral characteristics of greatest interest, rather than on the whole spectral range and/or for all spectral characteristics.

For example, if one wanted to compare, over the entire spectral range, a spectrum of an unknown sample acquired with a resolution of 1 $cm^{-1}$, with a database that contains, by way of example, 18000 reference spectra acquired with the same resolution, this comparison, using the methods of the state of the art, would require the evaluation of 65 million points.

Applicant has found that, by using the pre-calculated models according to the present invention, this comparison can require a number of evaluations of points between 20 and 80 times lower than the methods of the state of the art.

The use of pre-calculated models therefore allows to reduce in a correlated manner the necessary computing power, therefore excluding the need for remote data analysis and/or distributed computing, even in the presence of large databases.

This characteristic therefore allows to considerably increase the size of the databases to comprise a high number of classification groups, thus improving and extending the predictive and identification capabilities of the method of the present invention.

This characteristic also allows to work with spectra even at high resolution, improving the accuracy and precision of the method.

Moreover, for example, the presence of the list can make it superfluous to use least-squares methods and/or possible calculations of average square discards on the whole range of wave numbers for all the spectra.

In some embodiments, the analysis step E provides a plurality of comparative sub-steps in succession, in which the spectrum of the unknown sample is compared with the pre-calculated models.

In particular, each sub-step compares the spectrum of the unknown sample with the pre-calculated models of progressively smaller classification groups and supplies at least some scores showing the belonging of the unknown sample to microorganism classification groups of microorganism.

In some embodiments of the present invention, statistical and/or chemometric methods of multivariate analysis can be used for the comparison, such as for example Principal Components Analysis (PCA), or Linear Discriminant Analysis (LDA), also Linear Discriminant partial least-squares (LDPLS), Quadratic Discriminant Analysis (QD), Hierarchical Cluster Analysis (HCA), Random Forest, or any combination whatsoever of these and other techniques, not expressly mentioned.

In some embodiments, methods, techniques or algorithms that implement approaches based on neural networks can be used for said comparison.

In some embodiments, methods, techniques or algorithms that implement approaches based on artificial learning (machine learning) can be used for said comparison.

In some embodiments of the present invention, said comparison can also provide to compare the derivatives, first and/or second, of the spectra and of the models.

In some embodiments, it is possible to use statistical weights to weigh different regions of the spectra in different ways.

In some embodiments of the present invention, the comparison between spectra and model can be performed by means of a definition of distance between spectra and model, for example using methods based on least-squares.

In some embodiments, the distance can be used as a metric to perform statistical and/or chemometric analyses.

In some embodiments, the variance between spectra can be used for the PCA and/or LDA analysis.

In some embodiments, combined statistical methods can be used, which provide to perform a PCA, followed by the analysis of the linear discriminant of the main components, by means of LDA.

In these embodiments, when the result of the PCA is subjected to the subsequent LDA analysis, the separation of the clusters obtained by PCA is accentuated, allowing to also identify species that have very similar spectral characteristics to each other.

In some embodiments, the comparison sub-steps can provide to compare first the unknown spectrum with the pre-calculated models of the broader classification groups, in order to identify the broader category and/or classification group to which the unknown sample belongs; subsequently, the unknown spectrum is compared with the pre-calculated models of the progressively smaller classification groups, in order to identify the progressively smaller classification groups to which the unknown sample belongs.

Advantageously, this characteristic allows to perform a lower number of comparisons between types of spectra, with respect to other known methods.

For example, if the database contains 45 types of spectra associated with 45 different species, a method of the known state of the art would try to identify the unknown sample by comparing it with all the 45 types of species present.

In embodiments of the method of the present invention, on the other hand, the 45 species can be classified according to broader classification macro-groups (for example 4), characterized by similar characteristics.

Each macro-group contains, for example, 3 smaller classification groups, each of which in turn contains 2 further smaller classification sub-groups, the latter for example associated with different species or subspecies.

In this case, 3 sub-steps can be provided, wherein in the first sub-step the first classification macro-group is assigned to the unknown sample, in the second sub-step the second classification group is assigned, in the third sub-step the third classification group is assigned.

Advantageously, this characteristic allows to divide the spectra into similar macro-groups, simplifying the data matrix and allowing, after the first step, to work with a less complex data matrix, in which it is easier to identify the peculiarities that divide for example particularly similar species or subspecies.

Moreover, this characteristic therefore allows to obtain a faster and more efficient method, both in terms of time and also in terms of consumption of computing resources with respect to known methods.

In some embodiments, in each comparison sub-step, the multivariate analysis techniques supplies scores showing the belonging to each of the classification groups with which the unknown spectrum is compared.

The belonging scores can be obtained in a known manner from the multivariate analysis techniques as above and can possibly be normalized and expressed as percentages.

For example, in some embodiments, the belonging score can be associated with the linear discriminant between the main components.

In some embodiments, the control step F provides to verify the reliability of the identification performed in the analysis step E.

This control can be performed for example by verifying that in each sub-step at least one classification group to which the unknown sample belongs has been identified, which has a belonging score higher than a predetermined acceptance value, for example higher than 70%.

In this case, (block G in FIG. 2), the unknown sample is identified with the smaller classification group.

If in one or more comparison sub-steps one of the belonging scores is lower than the predetermined acceptance value, the method provides a second acquisition step C, a second processing step D and a second analysis step E to be carried out on a second assay taken from the unknown sample.

If the two analysis steps E assign the unknown sample to the same classification groups (block H in FIG. 2) the unknown sample is identified with the smallest classification group assigned by the two analysis steps E.

Otherwise, it is provided that a third assay is taken, and a third acquisition step C, a third processing step D and a third analysis step E are performed.

If the third analysis step E assigns the unknown sample to the same classification groups of at least one of the previous analysis steps E (block I in FIG. 2), the unknown sample is identified with the smallest classification group assigned by the two analysis steps E with matching results.

Otherwise, a message of non-identification is supplied (block J in FIG. 2).

One embodiment provides a computer program, or software, used to collect the data and analyze them with respect to the database, which can be memorized in a computer-readable medium and which contains instructions which, once executed by an analysis apparatus for the classification and identification of microorganisms, determine the execution of the method according to the present description.

Example 1

Figure 4A:
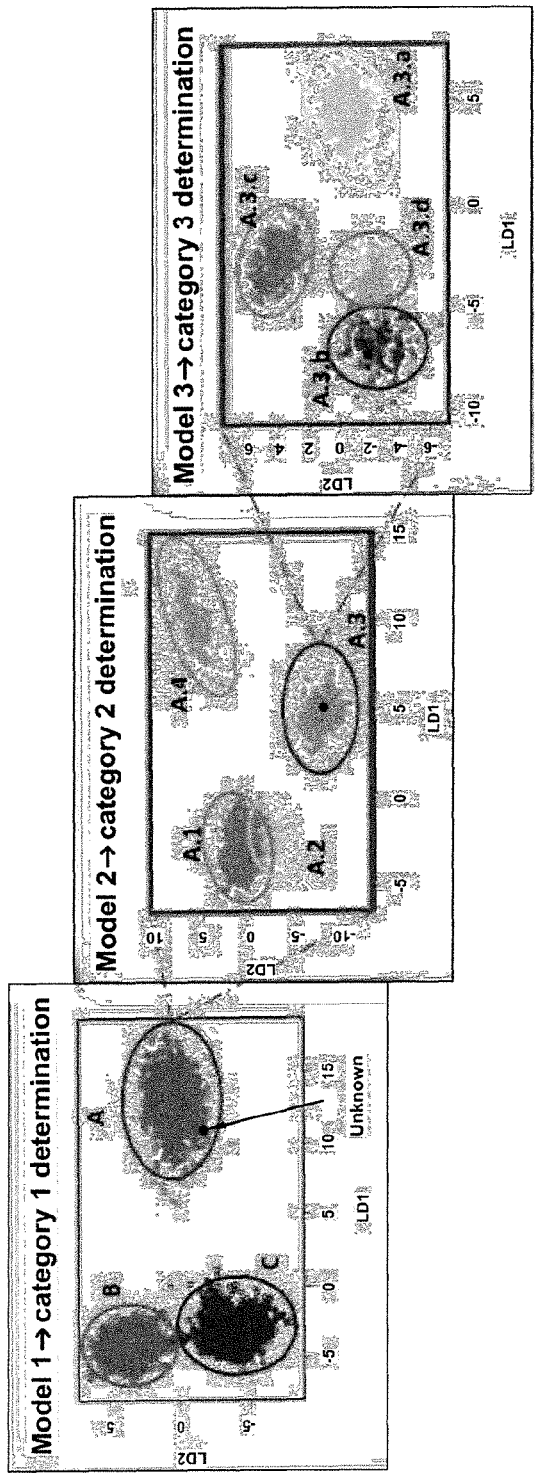
FIGS. 4a and 4b show, respectively, the graphic representation of sub-steps for a classification of an unknown sample obtained with step E, and the corresponding table to assign the score generated by step F for the reliability of the identification.

FIG. 4a schematically shows the process flow performed on an unknown spectrum to subsequently determine various categories of interest, by applying a plurality of predictive models (step E) in accordance with the present invention. The unknown spectrum is compared with a plurality of predictive models developed in steps A1, A2, A3, A4 on a database of known spectra. Each model is based, for example, on a PCA-LDA analysis for the attribution of a specific type among those possible for the category being determined. In particular, for each panel in FIG. 4a each point corresponds to the coordinates assigned by the PCA-LDA calculation to a spectrum present in the database of known samples (step A4); each point within a set A, B, C, reflects the specific type to which it belongs for the category being determined. In model 1, in which the belonging to the various types provided for category 1 is determined, all the spectra of known samples are grouped in the respective sets of belonging A, B, C (first panel of FIG. 4a). For model 1, three different types are therefore possible, each associated with a specific portion of the space defined by the model.

For each unknown spectrum, in step E the spatial coordinates that it takes in the space defined by the model are predicted, and by evaluating its disposition in the same space the type relating to the category in question is determined. By way of example, in the first panel of FIG. 4a it can be seen that for model 1, its coordinates are analogous to those of the spectra of the model belonging to type A and therefore it is assigned the same type.

The hierarchical subdivision of the models from the broadest to the smallest allows, by means of sub-steps that provide the application of a plurality of models, to obtain more and more specific information with respect to the type of microorganism in question (second and third panel of FIG. 4a).

It should be noted that belonging to a specific type within those provided for category 1 determines which will be the subsequent model to apply to the unknown sample.

The unknown spectrum is therefore compared with the pre-calculated models of progressively smaller classification groups, in order to identify progressively more detailed categories of belonging with which to associate the unknown sample (FIG. 4a).

For each model, applied in the analysis step E of the unknown sample, the score showing the belonging to the associated type is also calculated, possibly in the form of a percentage. This value reflects how much the coordinates calculated for the unknown spectrum are similar to those defined in the model for spectra of the same category (table in FIG. 4b).

Figure 4B:
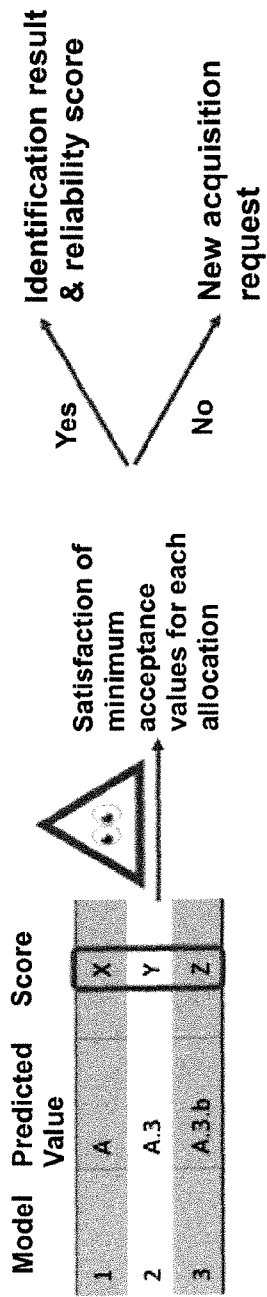

Subsequently, in step F, shown schematically in FIG. 4b, the belonging scores associated with each of the types determined during the various sub-steps of the process are evaluated, in order to evaluate the reliability of the result. For each model, acceptance values have been defined, above which the result can be considered reliable. If from the comparison above, it emerges that all the values of the belonging scores are higher than those preestablished for each model, a result is supplied (step G), otherwise a new analysis step is requested.

Example 2

In one embodiment of the method, it can be used to identify any one whatsoever of the possible taxonomic characteristics described above, such as for example the Genus of microorganisms. See FIG. 5, which shows a confusion matrix obtained from the validation of the method with the spectra of a database according to the present invention, in which a correspondence from 97.5% to 100% can be observed between the actual and the predicted result.

It is clear that modifications and/or additions of parts or steps can be made to the method and/or apparatus as described heretofore, without departing from the field and scope of the present invention. It is also clear that, although the present invention has been described with reference to some specific examples, a person of skill in the art shall certainly be able to achieve many other equivalent forms of method and/or apparatus, having the characteristics as set forth in the claims and hence all coming within the field of protection defined thereby.

The invention claimed is:

1. A method of identifying microorganisms in a sample, by evaluating the vibrational profile, comprising:
    a step of preparing a database of reference spectra of known samples of known microorganisms comprising:
    one or more steps of sampling a known sample;
    one or more steps of acquiring the spectrum of the known sample;
    one or more steps, possibly automated, of processing the spectrum of the known sample in order to at least identify spectral regions in which to evaluate the presence of spectral characteristics identifying each category and/or classification group;
    one or more steps of creating a plurality of pre-calculated models, associated with categories and/or classification groups of hierarchically organized microorganisms, from broader categories and/or classification groups to smaller categories and/or classification groups, each pre-calculated model comprising said identification spectral characteristics associated with a category and/or a classification group of microorganisms;
    a step of sampling an unknown sample;
    one or more steps of acquiring the spectrum of the unknown sample;
    one or more steps of processing the spectrum of the unknown sample on the basis of what is defined in step;
    one or more analysis steps, each of which provides to perform in succession a plurality of sub-steps of comparing the spectrum of the unknown sample with said pre-calculated models, each sub-step comparing, by means of multivariate analysis methods, the spectrum of the unknown sample with the pre-calculated models of progressively smaller categories and/or classification groups, in order to supply at least scores showing the belonging of the unknown sample to said categories and/or classification groups of microorganism;
    one or more control steps in which a new acquisition step of the spectrum of the unknown sample is requested if said reliability parameters are lower than predetermined acceptance values, or a final result of the method is supplied, which can comprise a failed identification, or a successful identification.

2. The method as in claim 1, wherein said control step provides to verify that in each of said comparison sub-steps at least one classification group has been identified to which the unknown sample belongs, which has a belonging score higher than said predetermined acceptance value.

3. The method as in claim 1, wherein the step of creating a plurality of pre-calculated models provides to use combined statistical methods, which provide to perform an analysis of the main components, followed by the analysis of the linear discriminant of the main components, then applying the pre-calculated models in order to predict the categories and/or classification groups in the step of analyzing the unknown sample.

4. The method as in claim 1, wherein the unknown sample and/or the known sample is grown using any suitable culture medium whatsoever, in the presence or absence of biological fluids and/or complex matrices.

5. The method as in claim 1, wherein the unknown sample and/or the known sample is a sample directly obtained from a native sample not subjected to the growth phase.

6. The method as in claim 1, wherein the analysis step provides to use methods based on neural networks.

7. The method as in claim 1, wherein the steps provide a continuous acquisition mode both in the absence and also in the presence of a sample, the continuous mode assisting respectively the cleaning operations of the instrument and the objective evaluation of the spectral parameters preparatory to the standardized acquisition of the spectrum.

8. The method as in claim 7, wherein said spectral parameters are signal intensity, signal-to-noise ratio, spectral shape, optimum drying level.

9. An apparatus to carry out the method of identifying microorganisms in sample as in claim 1, comprising a device to detect the vibrational profile comprising a source of radiation, a detector, an acquisition zone being defined, on which the sample to be analyzed is positioned, and an electronic device, of the fixed or portable type coupled to the detection device, in which a processing system and a data display system are installed, wherein in said electronic device pre-calculated models are stored, associated with classification groups of hierarchically organized microorganisms, from broader classification groups to smaller classification groups, each pre-calculated model comprising identification spectral characteristics associated with a classification group of microorganisms, therefore not needing to connect to the Internet to perform the calculation operations necessary to obtain the result.

10. A computer program, or software, used to collect data and analyze them with respect to a database, which is storable in a medium readable by an electronic device and which contains the instructions that, once performed by an analysis apparatus for the classification and identification of microorganisms, determine the execution of the method as in claim 1.

* * * * *